(12) United States Patent
Dahri-Correia et al.

(10) Patent No.: US 8,241,620 B2
(45) Date of Patent: Aug. 14, 2012

(54) COMPLEX POLYMERE AMPHIPHILE-PDGF

(75) Inventors: Latifa Dahri-Correia, Saint Bonnet de Mure (FR); Jose Correia, Saint Bonnet de Mure (FR); Guy Dubreucq, Lille (FR); David Duracher, Lyons (FR); Remi Soula, Meyzieu (FR); Olivier Soula, Meyzieu (FR); Gerard Soula, Meyzieu (FR)

(73) Assignee: Adocia, Lyons (FR)

( * ) Notice: Subject to any disclaimer, the term of this patent is extended or adjusted under 35 U.S.C. 154(b) by 0 days.

(21) Appl. No.: 13/067,299

(22) Filed: May 23, 2011

(65) Prior Publication Data
US 2011/0301086 A1 Dec. 8, 2011

Related U.S. Application Data

(63) Continuation of application No. 11/526,735, filed on Sep. 26, 2006, now abandoned.

(30) Foreign Application Priority Data

Sep. 26, 2005 (FR) ..................................... 05 09803

(51) Int. Cl.
*A61K 31/74* (2006.01)
(52) U.S. Cl. .................................................. 424/78.17
(58) Field of Classification Search .................. None
See application file for complete search history.

(56) References Cited

U.S. PATENT DOCUMENTS

| 5,234,908 A | * | 8/1993 | Szabo et al. ................... 514/8.2 |
| 5,457,093 A | | 10/1995 | Cini et al. |
| 5,705,485 A | | 1/1998 | Cini et al. |
| 5,905,142 A | | 5/1999 | Murray |
| 7,683,024 B2 | * | 3/2010 | Chan et al. ................... 514/19.3 |
| 2002/0169120 A1 | | 11/2002 | Blanchat et al. |
| 2002/0183282 A1 | | 12/2002 | Dahricorreia et al. |
| 2008/0014250 A1 | | 1/2008 | Soula et al. |

FOREIGN PATENT DOCUMENTS

| EP | 0 859 596 B1 | 12/2001 |
| EP | 1 369 136 B1 | 8/2006 |
| EP | 2 007 816 | 12/2008 |
| JP | A-11-512740 | 11/1999 |
| WO | WO 93/08825 A1 | 5/1993 |
| WO | WO 97/12601 A2 | 4/1997 |
| WO | WO 00/76452 A2 | 12/2000 |
| WO | WO 00/76562 A1 | 12/2000 |
| WO | WO 02/058718 A2 | 8/2002 |
| WO | WO 03104303 A1 * | 12/2003 |
| WO | WO 2007013100 A1 | 2/2007 |
| WO | WO 2007/116143 A1 | 10/2007 |

OTHER PUBLICATIONS

C. Oefner et al., "Crystal Structure of Human Platelet-Derived Growth Factor BB," The EMBO Journal, vol. 11, No. 11, (1992) pp. 3921-3926.

(Continued)

*Primary Examiner* — Paul Dickinson
(74) *Attorney, Agent, or Firm* — Oliff & Berridge, PLC

(57) ABSTRACT

Physically and chemically stable, water-soluble, amphiphilic polymer-PDGF complex, characterized in that the amphiphilic polymers include a hydrophilic polymeric backbone functionalized with hydrophobic substituents and hydrophilic groups.

17 Claims, 1 Drawing Sheet

OTHER PUBLICATIONS

R. Ross et al., "A Platelet-Dependent Serum Factor That Stimulates the Proliferation of Arterial Smooth Muscle Cells in Vitro," Proc. Natl. Acad. Sci. USA, vol. 71, No. 4, (1974) pp. 1207-1210.

N. Kohler et al., "Platelets as a Source of Fibroblast Growth-Promoting Activity," Experimental Cell Research, vol. 87 (1974) pp. 297-301.

E. W. Raines et al., "Platelet-Derived Growth Factor in Vivo," Biology of Platelet-Derived Growth Factor, vol. 5, (1993) pp. 74-114.

R. Ross et al., "Localization of PDGF-B Protein in Macrophages in All Phases of Atherogenesis," Science, vol. 248, (1990) pp. 1009-1012.

D. Y. Tzeng et al., "Platelet-Derived Growth Factor Promotes Human Peripheral Monocyte Activation," Blood, vol. 66, No. 1, (1985) pp. 179-183.

G. P. Risbridger, "Discrete Stimulatory Effects of Platelet-Derived Growth Factor (PDGF-BB) on Leydig Cell Steroidogenesis," Molecular and Cellular Endocrinology, vol. 97, (1993) pp. 125-128.

E. Wilson et al., "Platelet-Derived Growth Factor Stimulates Phagocytosis and Blocks Agonist-Induced Activation of the Neutrophil Oxidative Burst: A Possible Cellular Mechanism to Protect Against Oxygen Radical Damage," Proc. Natl. Acad. Sci. USA, vol. 84, (1987) pp. 2213-2217.

R. A. Majack et al., "Induction of Thrombospondin Messenger RNA Levels Occurs as an Immediate Primary Response to Platelet-Derived Growth Factor," The Journal of Biological Chemistry, vol. 262, No. 18, (1987) pp. 8821-8825.

N. Morisaki et al., "Platelet-Derived Growth Factor is a Potent Stimulator of Expression of Intercellular Adhesion Molecule-I in Human Arterial Smooth Muscle Cells," Biochemical and Biophysical Research Communications, vol. 200, No. 1, (1994) pp. 612-618.

H. P. Lorenz et al., "Essential Practice of Surgery," Springer, Chapter 7, (2003) pp. 77-88.

R. Lobmann et al., "Expression of Matrix Metalloproteinases and Growth Factors in Diabetic Foot Wounds Treated with a Protease Absorbent Dressing," Journal of Diabetes and Its Complications, vol. 20, (2006) pp. 329-335.

G. Lauer et al., "Expression and Proteolysis of Vascular Endothelial Growth Factor is Increased in Chronic Wounds," The Journal of Investigative Dermatology, vol. 115, No. 1, (2000) pp. 12-18.

D. R. Yager et al., "Wound Fluids from Human Pressure Ulcers Contain Elevated Matrix Metalloproteinase Levels and Activity Compared to Surgical Wound Fluids," The Journal of Investigative Dermatology, vol. 107, No. 5, (1996) pp. 743-748.

B. Cullen et al., "The Role of Oxidised Regenerated Cellulose/Collagen in Chronic Wound Repair and its Potential Mechanism of Action," The International Journal of Biochemistry & Cell Biology, vol. 34, (2002) pp. 1544-1556.

D. G. Greenhalgh et al., "PDGF and FGF Stimulate Wound Healing in the Genetically Diabetic Mouse," American Journal of Pathology, vol. 136, No. 6, (1990) pp. 1235-1246.

D. Ladin, "Becaplermin Gel (PDGF-BB) as Topical Wound Therapy," (Safety and Efficacy Report) Plastic and Reconstructive Surgery, vol. 105, No. 3, (2000) pp. 1230-1231.

G. A. Holloway et al., "A Randomized, Controlled, Multicenter, Dose Response Trial of Activated Platelet Supernatent, Topical CT-102 in Chronic, Nonhealing, Diabetic Wounds," Wounds: A Compendium of Clinical Research and Practice, vol. 5, No. 4, (1993) pp. 198-206.

V. J. Mandracchia et al., "The Use of Becaplertnin (rhPDGF-BB) Gel for Chronic Nonhealing Ulcers," Clinics in Podiatric Medicine and Surgery, vol. 18, No. 1, (2001) pp. 189-209.

T. J. Weiman, "Clinical Efficacy of Becaplermin (rhPDGF-BB) Gel," The American Journal of Surgery, vol. 176 (Suppl. 2A), (1998) pp. 74S-79S.

F. Grinnell et al., "Fibronectin Degradation in Chronic Wounds Depends on the Relative Levels of Elastase, $\alpha 1$-Proteinase Inhibitor, and $\alpha 2$-Macroglobulin," The Journal of Investigative Dermatology, vol. 106, No. 2, (1996) pp. 335-341.

C. N. Rao et al., "$\alpha 1$-Antitrypsin Is Degraded and Non-Functional in Chronic Wounds But Intact and Functional in Acute Wounds: The Inhibitor Protects Fibronectin from Degradation by Chronic Wound Fluid Enzymes," The Journal of Investigative Dermatology, vol. 105, No. 4, (1995) pp. 572-576.

V. Falanga et al., "Topical Use of Human Recombinant Epidermal Growth Factor (h-EGF) in Venous Ulcers," J. Derm. Surg. Oncol., vol. 18, (1992) pp. 604-606.

D. R. Yager et al., "Ability of Chronic Wound Fluids to Degrade Peptide Growth Factors is Associated with Increased Levels of Elastase Activity and Diminished Levels of Proteinase Inhibitors," Wound Repair and Regeneration, vol. 5, No. 1, (1997) pp. 23-32.

M. Wlaschek et al., "Protease Inhibitors Protect Growth Factor Activity in Chronic Wounds," British Journal of Dermatology, vol. 137, (1997) pp. 646-662.

T. J. Wieman, "Efficacy and Safety of Recombinant Human Platelet-Derived Growth Factor-BB (Becaplermin) in Patients with Chronic Venous Ulcers: A Pilot Study," Wounds, vol. 15, No. 8, (2003) pp. 257-264.

C. Hart et al., "Purification of PDGF-AB and PDGF-BB from Human Platelet Extracts and Identification of All Three PDGF Dimers in Human Platelets," Biochemistry, vol. 29, (1990) pp. 166-172.

C. H. Heldin, "Structural and Functional Studies on Platelet-Derived Growth Factor," The EMBO Journal, vol. 11, No. 12, (1992) pp. 4251-4259.

E. W. Raines et al., "Platelet-Derived Growth Factor," The Journal of Biological Chemistry, vol. 257, No. 9, (1982) pp. 5154-5160.

H. N. Antoniades, "Human Platelet-Derived Growth Factor (PDGF): Purification of PDGF-I and PDGF-II and Separation of Their Reduced Subunits," Proc. Natl. Acad. Sci. USA, vol. 78, No. 12, (1981) pp. 7314-7317.

T. F. Deuel et al., "Human Platelet-Derived Growth Factor," The Journal of Biological Chemistry, vol. 256, No. 17, (1981) pp. 8896-8899.

G. Wei et al., "Nano-Fibrous Scaffold for Controlled Delivery of Recombinant Human PDGF-BB," Journal of Controlled Release, vol. 112, (2006) pp. 103-110.

Carion et al., "Polysaccharide Microarrays for Polysaccharide-Platelet-Derived-Growth-Factor Interaction Studies," ChemBioChem, 2006, pp. 817-826, vol. 7.

Laetitia et al., "Effect of a Dextran Derivative Associated with TGF-Beta 1 or FGF-2 on Dermal Fibroblast Behaviour in Dermal Equivalents," Journal of Biomaterials Science Polymer Edition, 2004 (Abstract only).

International Search Report issued in International Application No. PCT/IB2006/002666; mailed on Jul. 27, 2007 (with English translation).

* cited by examiner

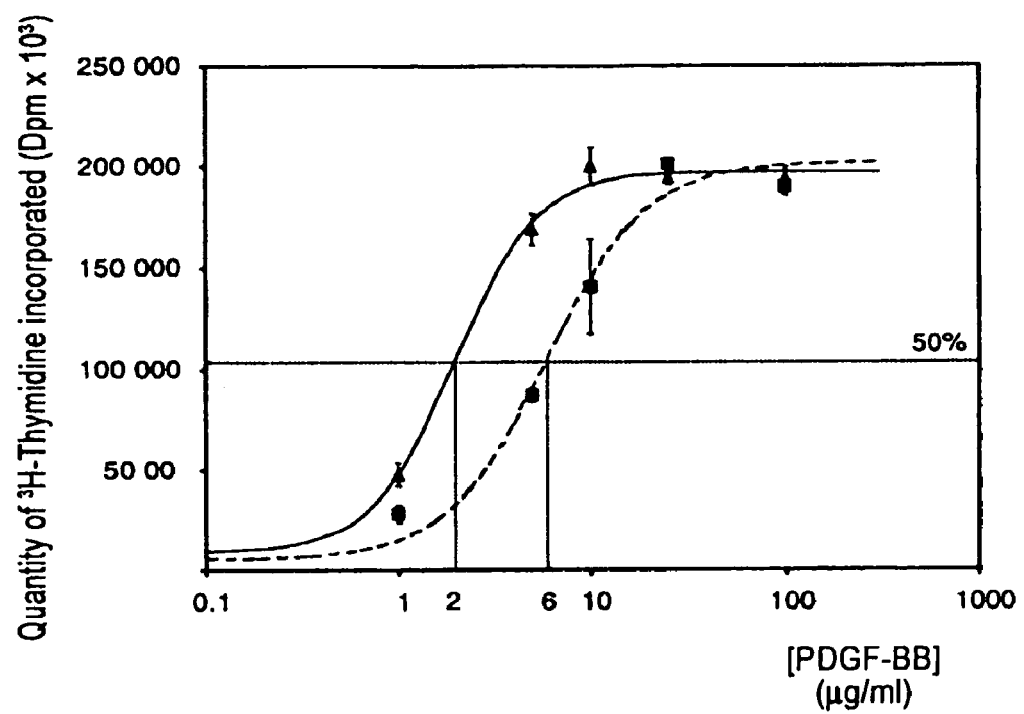

COMPLEX POLYMERE AMPHIPHILE-PDGF

This is a Continuation of application Ser. No. 11/526,735 filed Sep. 26, 2006. The disclosure of the prior application is hereby incorporated by reference herein in its entirety.

BACKGROUND

The present invention relates to novel complexes of platelet-derived growth factor (PDGF) associated with amphiphilic polymers for improving the physical and chemical stability, in vitro and in vivo, of the therapeutic protein for pharmaceutical applications.

PDGFs are glycoproteins of approximately 30 000 daltons, made up of two polypeptide chains linked to one another via two disulphide bridges. Four types of chains have been identified, A, B, C and D. The native protein exists in the form of a homodimer or of an AB-type heterodimer (Oefner C. EMBO J. 11, 3921-2926, 1992).

PDGF was isolated for the first time from platelets. PDGFs are growth factors released during blood clotting, capable of promoting the growth of various cell types (Ross R. et al., Proc. Natl. Acad. Sci. USA, 1974, 71, 1207; Kohler N. & Lipton A., Exp. Cell Res., 1974, 87, 297). It is known that PDGF is produced by a certain number of cells other than platelets, and that it is mitogenic with respect to most of the cells derived from the mesenchyma, i.e. blood, muscle, bone and cartilaginous cells, and also connective tissue cells (Raines E. W., in "*Biology of Platelet-Derivated Growth Factor*", 1993, Westermark, B. and C. Sorg, Ed. Basel, Kerger, p. 74). Many articles tend also to demonstrate that macrophage-derived PDGF behaves like a chemotactic and mitogenic agent with respect to smooth muscle cells, and that it contributes to the myointimal thickening of arterial walls characteristic of arteriosclerosis (Ross R. et al., Science, 1990, 248, 1009). The activities of PDGF include, in addition and in particular, the stimulation of granule release by neutrophilic monocytes (Tzeng D. Y. et al., Blood, 1985, 66, 179), the facilitation of steroid synthesis by Leydig cells (Risbridger G. P., Mol. Cell, Endocrinol., 1993, 97, 125), the stimulation of neutrophil phagocytosis (Wilson E. et al., Proc. Natl. Acad. Sci. USA, 1987, 84, 2213), the modulation of thrombospondin expression and secretion (Majak R. A. et al., J. Biol. Chem., 1987, 262, 8821), and the post-regulation of the ICAM-1 gene in vascular smooth muscle cells (Morisaki N. et al., Biochem. Biophys. Res. Commun., 1994, 200, 612).

Given these various properties, the use of recombinant PDGFs in the pharmaceutical field has already been envisaged. The use of PDGF has in particular been approved for the treatment of diabetic foot ulcers (Regranex, J&J) and for periodontal repair (GEM 21S, Biomimetic).

Ulcer healing, just like cutaneous healing in general, is a complex phenomenon that requires the coordinated intervention, over time and in space, of numerous cell types, that can be summarized in three phases: an inflammation phase, a proliferation phase and a remodeling phase.

In the inflammation phase, which is approximately 7 days for normal healing, macrophages kill the bacteria, debride damaged tissues and regenerate the tissues. To do this, the macrophages secrete collagenases, cytokines and growth factors.

In the course of the proliferation phase, which is from the $3^{rd}$ day to the $3^{rd}$ week for normal healing, three events follow on from one another. The wound fills with granulation tissue, angiogenesis develops and the wound becomes covered with epithelial cells. The granulation tissue grows from the edges to the centre. Fibroblasts abundantly produce collagen type III.

In the course of the remodeling, which is from the $3^{rd}$ week to 1 or even 2 years, the granulation tissues mature, and the fibroblasts produce less collagen. The blood vessels formed during the granulation that are of no use are eliminated by apoptosis. The collagen type III is replaced with collagen type I, which organizes according to lines of tension and crosslinks.

In this process, PDGF plays an essential role. During the formation of a wound, platelets aggregate and release PDGF. The PDGF attracts neutrophils, macrophages and fibroblasts to the wound and is a potent mitogen. The macrophages and the endothelial cells in turn synthesize and secrete PDGF. The PDGF stimulates the production of the new extracellular matrix by the fibroblasts, essentially the non-collagen compounds such as glycosaminoglycans and the adhesion proteins (J. F. Norton et al, Essential practice of surgery, Springer, 2003, chapter 7, 77-89).

Chronic wounds such as diabetic foot ulcers, venous ulcers and pressure ulcers have the particularity of healing very slowly and sometimes incompletely because the healing process does not take place normally (R. Lobmann et al., J. of Diabetes and its complications, 2006, 20, 329-335).

The healing process is in fact a delicate balance between a process of destruction necessary in order to eliminate the damage to tissues and the repair process that results in the formation of new tissues. Proteases and growth factors play an essential role in this process by regulating this balance. In the case of chronic wounds, this balance is disturbed in favour of degradation, therefore these wounds are slow to heal. Although different types of chronic wounds exist, they are biochemically relatively similar in the sense that they are characterized by sustained inflammation phases that result in high levels of proteases and thus decrease growth factor activity (G. Lauer et al. J. Invest. Dermatol. 115 (2000) 12-18). This growth factor degradation contributes to an overall loss of tissues associated with these chronic wounds that does not favour healing (D. R. Yager et al., J. Invest. Dermatol. 107 (1996) 743-748).

There currently exists on the market a human recombinant PDGF-BB-based medicament corresponding to the international non-proprietory name "becaplermin", sold under the trade name Regranex®. This medicament is indicated for the treatment of lower limb ulcers in diabetics. It is in the form of a gel for topical application and makes it possible to promote ulcer healing. It makes it possible in particular, just like endogenous PDGF, to promote cell proliferation and therefore the formation of new tissues.

This treatment has a limited efficacy (Cullen et al. The international journal of biochemistry & Cell Biology 34, 1544-1556, 2002) even though the clinical studies have shown improvements in healing and in the period of time required for healing (Greenhalgh et al., American Journal of pathology, 136, 1235-1246 1990; Ladin Plastic and Reconstructive Surgery, 105, 1230-1231 2000; Holloway et al. Wounds, 5/4, 198-206; Mandracchia et al. Clinics in Podiatric Medicine and Surgery, 18, 189-209 2001; Wieman T. J. American Journal of Surgery, 176, 74S-79S 1998).

The Regranex product that contains PDGF-BB, sold by J&J, has demonstrated its efficacy by increasing the rate of recovery, in the patients treated, to 50% against only 36% for patients who only received standard treatment of the wound. Despite this significant improvement in the treatment of diabetic foot ulcers, it must be noted that only 50% of the patients experience recovery after a long and expensive treatment. In the cases of non-recovery, the consequences can be extremely serious and, in many cases, result in amputation of the lower limb. It should be added that the average duration of the treatment is very long, approximately 20 weeks, and the application thereof is expensive and restrictive because the wound must be cleaned and Regranex applied in the morning, followed 12 hours later, by cleaning of the wound. These two procedures most commonly require care by a nurse. In addition, the average cost of a treatment lasting twenty weeks is excessively high (of the order of 1400 American dollars).

The partial efficacy can be explained by a rapid degradation of the PDGF on the wound to be treated. This degradation results, in the case of a chronic wound, from a sustained inflammation state generating, at the wound, an environment hostile to the PDGF due to the stimulation of an overproduction of proteases.

Although degradation control is necessary for wound healing, excessive proteolytic activity is harmful since it leads to degradation of the extracellular matrix (F. Grinnell et al. J. Invest. Dermatol. 106 (1996) 335-341 and C. N. Rao et al. J. Invest. Dermatol. 105 (1995) 572-578) and of molecules that have a key functional role such as growth factors (V. Falanga et al. J. Derm. Surg. One. 18 (1992) 604-606; D. R. Yager et al. Wound Rep, Reg. 5 (1997) 23-32. and M. Wlaschek et al. Br. J. Dermatol. 137 (1997) 646-647). In fact, growth factors such as PDGF, TGFβ or bFGF are key elements in the healing process due to their abilities to induce cell migration, proliferation, protein synthesis and matrix formation and, more generally, due to the fact that they control the repair process. However, these growth factors are protein molecules and, consequently, are sensitive to proteolytic degradation. Several studies show that the degradation of growth factors such as PDGF is much more rapid when they are brought into contact with fluids originating from chronic wounds since they contain high concentrations of metalloproteinases (D. R. Yager et al. J. Invest. Dermatol. 107 (1996) 743-748).

For the treatment of venous ulcers, Regranex, in a pilot clinical study reported in the publication (T. J. Wieman, Wounds, 2003, vol. 15, No. 8, 257-264), showed only a minor improvement of current treatments based on regular cleaning of the wound with compression therapy.

The problem of the instability of PDGF, for example, was revealed during the production of the protein. It is known that PDGF is particularly sensitive to post-translational proteolysis (Hart et al., Biochemistry 29:166-172, 1990 and U.S. patent Ser. No. 07/557,219) and especially at the level of the bond between the arginine amino acid at position 32 and the threonine amino acid at position 33 of the mature chain of the protein. Other sites are sensitive to proteolysis, such as the bond between the arginine at position 79 and the lysine at position 80, or else the bond between the arginine at position 27 and the arginine at position 28 of the B chain of PDGF.

This proteolytic instability poses a major problem in the context of obtaining this protein, which is produced in a recombinant manner in yeast according to the method described in U.S. Pat. No. 4,845,075. Specifically, U.S. Pat. No. 7,084,262 teaches us that the analysis and purification of PDGF-BB leads to the production of 21 isoforms resulting from post-translational endoproteolytic cleavages. This great structural heterogeneity consequently results in a 50% decrease in the activity of the protein produced by genetic engineering compared with the intact protein in mature form.

Moreover, recent clinical results by Cardium, according to a press communiqué dated 14 Aug. 2006 (www.prnewswire.com) on diabetic foot ulcers that have not recovered after 14 weeks, shows the potential that a treatment with PDGF-BB can offer. The solution proposed by Cardium consists in introducing the gene for expression of PDGF-BB into the cells of the wound so as to overexpress it locally. This gene therapy by means of an adenovector made it possible to heal close to 80% of these diabetic foot ulcers resistant to the common treatments, out of a group of 15 patients. This therapeutic solution is promising. However, pharmaceutical developments of gene therapy-based treatments are, to date, still very hazardous for reasons of safety linked to the use of adenovirus-type viral vectors.

There is therefore a need and the possibility to improve the current treatments for diabetic foot ulcers, with PDGF.

In the case of diabetic foot ulcer treatment, the final objective is three-fold:
to accelerate recovery
to increase the rate of recovery
to simplify the treatment protocol.

There is also the case of venous ulcers and of pressure ulcers, which are the cause of considerable pain and of very serious medical complications.

The problem to be solved is therefore essentially that of protecting PDGF on chronic wounds.

Various solutions have been proposed.

U.S. Pat. No. 5,905,142 describes a means of remedying these proteolysis problems concerning PDGF by generating mutants of the protein that have an increased resistance with respect to proteolytic attacks, by substituting or by deleting one or more lysine or arginine amino acids close to the potential cleavage sites. This strategy for making the protein more resistant to proteases is not satisfactory. This genetic modification of PDGF can lead to modifications of the biological activity, with affinities that are different with respect to its various receptors, which can also induce toxicological problems. In addition, such a modification of PDGF requires a new pharmaceutical development, which is extremely expensive and risky.

In the 1970s, when this protein was abundantly studied, it was found that purification was extremely tricky since PDGF is "a very sticky protein" due to its cationic and hydrophobic properties (Heldin, C. H. EMBO J. 11:4251-4259, 1992; Raines and Ross, J. Biol. Chem. 257(9):5154-5160, 1982; Antoniades, PNAS 78:7314, 1981; Deuel et al. J. Biol. Chem. 256:8896, 1981). PDGF is in fact a highly cationic protein, the isoelectric point of which is between 9.8 and 10.5. Other authors confirm this behaviour, such as Wei et al. (Journal of controlled release 112:103-110, 2006), who explain that PDGF readily adsorbs onto surfaces of the container in which it is in solution. The authors solve the problem by adding, to the mixture, either 0.1% BSA or a 0.1% BSA/Tween 20 mixture. These solutions solve the problems to a large extent since up to 95% of the protein is found in solution. However, these solutions are not satisfactory from a pharmaceutical point of view, given the animal origin of the BSA and the risks related to bovine spongiform encephalopathy.

Another solution proposed by the same authors consists in adding a more powerful anionic surfactant (SDS), that makes it possible to maintain the PDGF in solution. Unfortunately, SDS also induces partial denaturation of the protein, resulting in a loss of bioactivity. This solution is not therefore satisfactory for stabilizing the protein.

In patent WO 93/08825, the inventors have demonstrated that purified PDGF exhibits great instability when it is formulated in the form of a gel for topical application. They give, as an example, the incompatibility of PDGF with a certain number of products conventionally used for formulating pharmaceutical products, such as methylcellulose or hydroxypropylcellulose, and also certain conventional preserving agents such as benzyl alcohol. The authors pose the problem by explaining that there exists a need to formulate PDGF in the form of a gel for topical administration while at the same time having good long-term stability. The same authors show that PDGF in solution degrades due to a process of deamidation at neutral pH and that the protein is more stable at a slightly acidic pH. The authors show that, by combining several parameters, a polymer that does not exhibit any interactions with the protein, a buffer at slightly acidic pH making it possible to limit the deamidation reaction and a preserving agent that is neutral with respect to the protein, it is possible to formulate the PDGF in order to obtain a formulation that is stable from a pharmaceutical point of view.

The authors show that it is possible to obtain a storage-stable formulation through the addition of a polymer that does not exhibit any interactions with the protein, with the proviso that the formulation is maintained at a slightly acidic pH in order to avoid reactions that degrade the protein by deamidation. This solution is not, however, satisfactory since it does not make it possible to protect the growth factor against proteolytic degradations in vivo at physiological pH.

In patent WO 97/12601, which describes PDGF formulations in the form of a gel, the authors explain that the cellulose derivative that they use is capable of stabilizing growth factors against a possible loss of activity during storage. For this, they use the results obtained previously on EGF in U.S. Pat. No. 4,717,717 as a basis. However, they also explain that the stability of the cellulose gel containing PDGF can be greatly improved by adding to the formulation a charged chemical species such as charged amino acids or metal ions. Here again, this solution makes it possible to stabilize the growth factors in the formulation during the storage of the product, but does not allow a stabilization of these growth factors with respect to the proteases present in chronic wounds at physiological pH.

SUMMARY

There exists therefore a therapeutic advantage in stabilizing and protecting growth factors, in particular PDGF, in order to increase its efficacy in the context of a chronic wound treatment, and more particularly the treatment of diabetic foot ulcer wounds. The invention therefore relates to the stabilization of PDGF with respect to chemical or physical degradations that may occur at physiological pH in vitro and in vivo, by developing a complex between an amphiphilic polymer and a PDGF.

The invention therefore relates to the formation of a complex between an amphiphilic polymer and a PDGF (amphiphilic polymer-PDGF), this complex providing the protein with chemical and physical stabilization with respect to degradations at physiological pH in vitro and in vivo.

The present invention therefore relates to a physically and chemically stable, water-soluble, amphiphilic polymer-PDGF complex, characterized in that:
the amphiphilic polymers consist of a hydrophilic polymeric backbone functionalized with hydrophobic substituents and hydrophilic groups according to the following general formula:

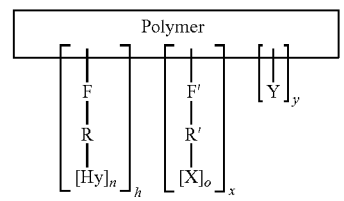

DP=m monomer units
R and R' being a bond or a chain comprising between 1 and 18 carbons, optionally branched and/or unsaturated comprising one or more heteroatoms, such as O, N and/or S,
R and R' being identical to or different from one another,
F and F' being an ester, a thioester, an amide, a carbonate, a carbamate, an ether, a thioether, an amine,
F and F' being identical to or different from one another,
X being a hydrophilic group that may be:
  a carboxylate
  a sulphate
  a sulphonate
  a phosphate
  a phosphonate,
Y being a hydrophilic group that may be:
  a sulphate
  a sulphonate
  a phosphate
  a phosphonate,
Hy being a hydrophobic group that may be:
  a $C_8$ to $C_{30}$ linear or branched alkyl, optionally unsaturated and/or containing one or more heteroatoms, such as O, N or S,
  a $C_8$ to $C_{18}$ linear or branched alkylaryl or arylalkyl, optionally unsaturated and/or optionally containing a heteroatom,
  an optionally unsaturated $C_8$ to $C_{30}$ polycycle,
n and o are between 1 and 3,
h represents the molar fraction of hydrophobic unit relative to a monomeric unit of between 0.01 and 0.5,
x represents the molar fraction of hydrophilic groups relative to a monomeric unit, of between 0 and 2.0,
y represents the molar fraction of hydrophilic groups relative to a monomeric unit, of between 0 and 0.5;
the PDGF is chosen from the group of PDGFs (platelet-derived growth factors).

BRIEF DESCRIPTION OF THE DRAWING

FIG. 1 is a graphical representation of the quantity of incorporated $^3$H-Thymidine expressed as a function of the concentration of PDGF-BB.

DETAILED DESCRIPTION OF EMBODIMENTS

It relates to a complex characterized in that the PDGF is chosen from the group consisting of human recombinant PDGFs containing two B chains (rhPDGF-BB).

It relates to a complex characterized in that the PDGF is PDGF-BB.

The substituents of the amphiphilic polymers are distributed in a controlled manner or randomly. Among the polymers having a controlled distribution of substituents, mention may, for example, be made of block copolymers and alternating copolymers.

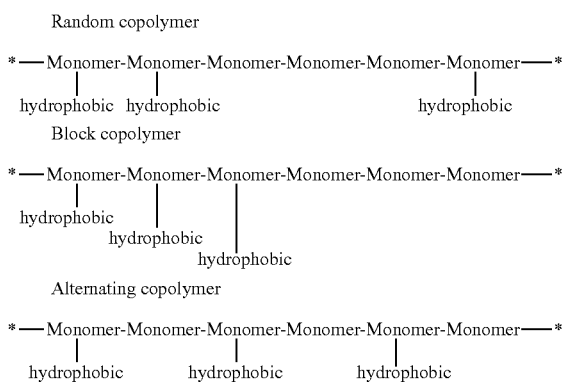

Thus, in one embodiment, the invention also relates to an amphiphilic polymer-PDGF complex characterized in that the polymer is chosen from polymers in which the substituents are distributed randomly.

In one embodiment, the invention also relates to an amphiphilic polymer-PDGF complex characterized in that the amphiphilic polymer is chosen from polyamino acids.

In one embodiment, the polyamino acids are chosen from the group consisting of polyglutamates or polyaspartates.

In one embodiment, the polyamino acids are homopolyglutamates.

In one embodiment, the polyamino acids are homopolyaspartates.

In one embodiment, the polyamino acids are copolymers of aspartate and glutamate. These copolymers are either block copolymers or random copolymers.

In one embodiment, the invention also relates to an amphiphilic polymer-PDGF complex characterized in that the polymer is chosen from polysaccharides.

In one embodiment, the polysaccharides are chosen from the group consisting of hyaluronans, alginates, chitosans, galacturonans, chondroitin sulphate, dextrans and celluloses.

The group of celluloses consists of celluloses functionalized with acids, such as carboxymethylcellulose.

The group of dextrans consists of dextrans functionalized with acids, such as carboxymethyldextran.

In one embodiment, the polysaccharide is a soluble dextran derivative corresponding to formula (I) below:

$$DMC_a B_b Su_c \quad (I)$$

in which:
D represents a polysaccharide chain, preferably consisting of series of glucoside units,
MC represents methylcarboxylic groups,
B represents N-benzylmethylenecarboxamide groups,
Su represents sulphate groups (sulphation of the free hydroxyl functions borne by the glucoside units),
a, b and c represent the degree of substitution (ds), respectively, of the groups MC, B and Su, with
i) a strictly greater than 0;
ii) b is such that:
either b is greater than or equal to 0.3 and c is between 0.1 and 0.5;
or b is strictly less than 0.3 and c corresponds to equation (1) below:

$$c \geq 8.5b^2 - 5.41b + 0.86 \quad (1).$$

These dextran derivatives of formula (I), and also the process for preparing them, are described more generally in patent application WO 99/29734. These dextran derivatives of formula (I) are trivially called DMCBSu and are considered to be copolymers consisting of R—OH and R—OX subunits, it being possible for X to be a methylcarboxylic (MC), benzylamide (B) or sulphate (Su) group. Thus, a methylcarboxylic dextran (DMC) with a degree of substitution (ds) of 0.6 in terms of methylcarboxylic groups contains 0.6 substituted group (R-MC) and 2.4 hydroxyl groups (ROH), per glucoside unit.

In one embodiment, D has a molar mass of between 1000 and 2 000 000 Da, and in one embodiment, less than 70 000 Da.

In one embodiment, the dextran derivatives are chosen from the compounds of formula (I) in which b is greater than or equal to 0.35.

In this case, and according to one embodiment, the dextran derivatives are chosen from the compounds of formula (I) in which a is between 0.5 and 0.8, and c is between 0.1 and 0.5.

In one embodiment, the polysaccharides are chosen from the group consisting of hyaluronans, alginates and chitosans.

These various polysaccharides may be represented as follows:

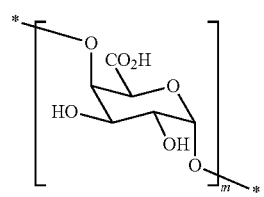

galacturonan

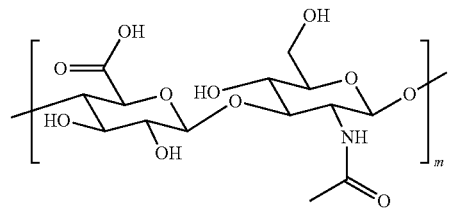

hyaluronan

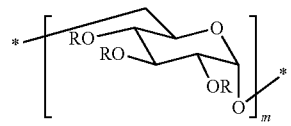

R═H, dextran
R═CH$_2$COOH or H, carboxymethyl dextran

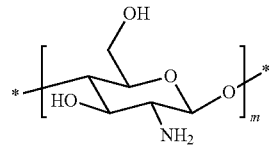

chitosan

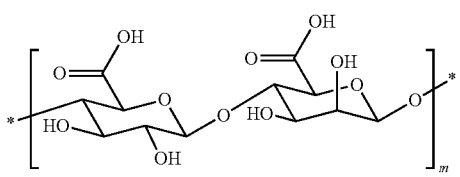

alginate

The polysaccharide may have an average degree of polymerization m of between 10 and 10 000.

In one embodiment, it has an average degree of polymerization m of between 10 and 5000.

In another embodiment, it has an average degree of polymerization m of between 10 and 500.

In one embodiment, the invention also relates to an amphiphilic polymer-PDGF complex characterized in that the hydrophobic group Hy is chosen from the group consisting of fatty acids, fatty alcohols, fatty amines, benzyl amines, cholesterol derivatives and phenols.

In one embodiment, the cholesterol derivative is cholic acid.

In another embodiment, the phenol is alpha-tocopherol.

In one embodiment, the amphiphilic polymer-PDGF complex according to the invention is reversible.

The polymers used are synthesized according to the techniques known to those skilled in the art, or are purchased from suppliers such as, for example, Sigma-Aldrich, NOF Corp. or CarboMer Inc.

The PDGFs are chosen from human recombinant PDGFs obtained according to the techniques known to those skilled in the art or purchased from suppliers such as, for example, from the companies Gentaur (USA) or Research Diagnostic Inc. (USA).

The demonstration of both chemical and physical stabilization can be carried out in particular by implementing the following tests:
- a test for demonstration of the amphiphilic polymer-PDGF complex according to the invention, carried out by gel electrophoresis (Gel Mobility Shift Assay);
- a test for slowing down of the enzymatic degradation of an amphiphilic polymer-PDGF complex according to the invention, carried out by bringing into contact with a protease;
- a test for physical stabilization of an amphiphilic polymer-PDGF complex according to the invention at physiological pH, carried out by SDS-Page.

The invention also relates to an amphiphilic polymer-PDGF complex characterized in that it passes the tests for demonstration of the chemical and physical stabilization, i.e. a test for demonstration of the complex (Gel Mobility Shift Assay), the test for slowing down of the enzymatic degradation by bringing into contact with a protease, and the test for physical stabilization at physiological pH carried out by SDS-Page.

The test for demonstration of the complex carried out by Gel Mobility Shift Assay is based on the displacement of ions under the effect of an electric field. The anionic complexes migrate to the anode and the cationic complexes are displaced to the cathode. After migration, the proteins are transferred by capillary action onto a PVDF membrane and visualized by means of an antibody specific for the protein, that is recognized by a peroxidase-coupled second antibody. The protein alone migrates little or not at all, the protein complex with the amphiphilic polymer migrates to the anode or the cathode depending on the overall charge of the complex.

The test for slowing down of the enzymatic degradation is based on verification of the integrity of the protein after the amphiphilic polymer-PDGF complex according to the invention has been brought into contact with a protease. A solution of a protease (trypsin, chymotrypsin, etc.) is added to the solution of complex and kinetics are determined. The reaction is stopped through the addition of an inhibitor specific for the enzyme (indole, benzamidine). The integrity of the protein is then analysed by polyacrylamide gel electrophoresis (SDS-Page).

The test for physical stabilization of a PDGF is based on verification of the integrity of the protein by comparison of a solution of the amphiphilic polymer-PDGF complex according to the invention with a solution of PDGF alone at pH 7.4, in terms of protein concentration in the solution. These two solutions are placed on a shaking bench for 48 h at ambient temperature and then centrifuged. The PDGF concentration in each of the solutions is evaluated by SDS-Page.

The amphiphilic polymer-PDGF complex according to the invention is formed by solubilizing a PDGF and an amphiphilic polymer in an aqueous solution at physiological pH without using any organic solvent that may denature the protein. The formation of the amphiphilic polymer-PDGF complex is spontaneous and does not involve any covalent bond between the PDGF and the amphiphilic polymer. This association takes place via weak bonds that are essentially hydrophobic interactions and ionic interactions.

The invention also relates to the method of preparing the amphiphilic polymer-PDGF complex according to the invention, characterized in that a PDGF and an amphiphilic polymer are brought into contact in solution at physiological pH.

Other tests can be set up in order to complete the demonstration of the formation of the amphiphilic polymer-PDGF complex according to the invention:
- a test for maintenance of the tertiary structure of the PDGF, determined by circular dichroism;
- a test for stability of a PDGF in the amphiphilic polymer-PDGF complex according to the invention at physiological pH under stress. The stress may be a specific method of agitation, the presence of salts, etc.

The invention also relates to an amphiphilic polymer-PDGF complex characterized in that the PDGF/amphiphilic polymer ratio is between 1/5 and 1/5000.

In one embodiment, it is between 1/100 and 1/5000.

In another embodiment, it is between 1/300 and 1/700.

The invention also relates to a therapeutic composition characterized in that it comprises an amphiphilic polymer-PDGF complex according to the invention.

The term "therapeutic composition" is intended to mean a composition that can be used in human or veterinary medicine.

The pharmaceutical composition according to the invention is preferably a composition for topical application that may be in the form of a gel, a cream, a spray, a paste or a patch.

The nature of the excipients that may be formulated with the amphiphilic polymer-PDGF complex according to the invention is chosen as a function of its presentation form, according to the general knowledge of the specialist in galenics.

Thus, when the composition according to the invention is in the form of a gel, the latter is, for example, a gel made from polymers such as carboxymethylcelluloses (CMCs), vinyl polymers, copolymers of PEO-PPO type, polysaccharides, PEOs, acrylamides or acrylamide derivatives.

Other excipients can be used in this invention in order to adjust the parameters of the formulation, such as a buffer for adjusting the pH, an agent for adjusting the isotonicity, preserving agents such as methyl para-hydroxybenzoate, propyl para-hydroxybenzoate, m-cresol or phenol, or else an antioxidant such as L-lysine hydrochloride.

According to the invention, the therapeutic composition is characterized in that it allows an administration of approximately 100 µg per ml of PDGF.

The present invention also relates to the use of an amphiphilic polymer-PDGF complex according to the invention, for the preparation of a therapeutic composition with healing action, for use in the treatment of ulcers by topical application.

It also relates to a method of therapeutic treatment for human or veterinary use, characterized in that it consists in administering, at the site of treatment, a therapeutic composition comprising the amphiphilic polymer-PDGF complex according to the invention.

EXAMPLES

Example 1

PDGF-BB/DMCBSu Complex

Synthesis of Sulphated Carboxymethyl Dextran Modified with Benzylamine (DMCBSu)

The amphiphilic polymer is synthesized from a carboxymethyl dextran having a degree of substitution, in terms of carboxymethyl per saccharide unit, of 1.0 and an average molar mass of 40 000 g/mol. The benzylamine is grafted onto the acids of this polymer according to a conventional method of coupling in water in the presence of a water-soluble carbodiimide. The degree of substitution, in terms of benzylamine per saccharide unit, is 0.4, determined by $^1$H NMR. This polymer is then sulphated with an $SO_3$/pyridine complex. The degree of substitution, in terms of sulphate per saccharide unit, is 0.3.

Preparation of the PDGF-BB/DMCBSu Complex

10 µl of a solution of PDGF-BB at 0.1 mg/ml is added to 90 µl of a solution of DMCBSu at 50 mg/ml. The PDGF-BB and DMCBSu solutions are buffered at pH 7.4 and 300 mOsm. This solution is gently stirred for two hours at ambient temperature and then stored at 4° C.

Demonstration of the Formation of a PDGF-BB/DMCBSu Complex

10 µl of the solution of the PDGF-BB/DMCBSu complex described above is loaded onto an agarose gel. The migration of the compounds is carried out under the effect of an electric field (200 mA—4 hours). After migration, the PDGF-BB is transferred onto a PVDF membrane overnight, and then visualized by immunoblotting with goat anti-PDGF-BB antibodies, to which will attach anti-goat IgG secondary antibodies coupled to HRP peroxidase, visualized by means of a substrate (5-bromo-4-chloro-3-indolyl phosphate/nitro blue tetrazolium).

The PDGF-BB/DMCBSu complex migrates to the anode. Its negative charge can be explained by the fact that it has a composition much more rich in DMCBSu than in PDGF-BB. The control, consisting only of PDGF-BB, does not migrate.

Demonstration of the stability of the solution of the PDGF/DMCBSu complex

10 µl of a solution of PDGF-BB at 0.01 mg/ml at pH 7.4 and 10 µl of the solution of the PDGF-BB/DMCBSu complex at pH 7.4 described above are placed on a shaking bench for 48 h at ambient temperature. After centrifugation, the PDGF-BB concentration in each of the solutions is evaluated by SDS-Page. It appears that the concentration of PDGF-BB in solution in the case of the PDGF-BB/DMCBSu complex has not changed, whereas that of the solution of PDGF-BB alone has decreased.

Demonstration of the protection of PDGF-BB against trypsin in this PDGF-BB/DMCBSu complex 10 µl of the solution of the PGDF-BB/DMCBSu complex described above are poured into 90 µl of a solution of trypsin at 10 ng/ml at 37° C.

A 10 µl sample is taken every 30 minutes and the concentration of PDGF-BB is measured by Elisa after having stopped the enzymatic reaction by adding 10 µl of a solution of indole at 10 µg/ml.

These kinetics reveal that the PDGF-BB alone is completely degraded in 1 h 30, whereas this is not the case in the PDGF-BB/DMCBSu complex.

Validation of the Biological Activity of the PDGF-BB/DMCBSu Complex

A primary culture of human dermal fibroblasts (Human Dermal Fibroblast adult (HDFa)) is realized at a temperature of 37° C. in αMEM medium with 10% of foetal calf serum (FCS) and 1% of penicillin-streptomycin in an atmosphere saturated with humidity and enriched in $CO_2$ (5%). The medium is renewed every 4 days. A dilution of the cell suspension in the culture medium was then realized in order to seed the culture dishes at a density of 5000 cells/well for 96-well plates (the company Nunc).

For each batch of cells, the PDGF-BB-stabilizing effect by means of the complex of various concentrations was verified by incorporation of tritiated thymidine (5000 cells/well in 100 µl). After withdrawal for 24 hours, the fibroblasts are stimulated by the addition of PDGF-B, at various concentrations ranging from 0.1 to 100 ng/ml, in the absence or presence of the amphiphilic polymer, at a concentration of 1 µg/ml. The tritiated thymidine incorporation is carried out 18 hours after the stimulation with PDGF-BB in the presence or absence of the complex, by the addition of a solution at 50 µCi/ml, i.e. 0.5 µCi/well. The radioactivity is recovered in counting vials, the wells are rinsed with 100 µl of 100 mM NaOH and the radioactivity is counted after the addition of 1 ml of scintillation fluid (Zinsser Analytic), on an automatic counter.

The results obtained are represented in the attached FIG. 1, in which the amount of tritiated thymidine incorporated by the fibroblasts (in Dpm×10$^3$) is expressed as a function of the concentration of PDGF-BB in µg/ml.

The solid-line curve represents the results of the complex according to the invention at a concentration of 1 µg/ml in terms of dextran derivative, and the dashed-line curve represents the results in the absence of the dextran derivative.

The ED50 corresponds to the concentration of PDGF-BB so as to have 50% proliferation of the human fibroblasts. The ratio R is the ratio of the ED50 values, calculated as follows:

$$R=ED50(PDGF\text{-}BB)/ED50(PDGF\text{-}BB+DMCBSu)$$

These results show that, when the PDGF-BB is used alone, it is necessary to use 6 µg/ml thereof in order to obtain 50% proliferation, whereas, when the PDGF-BB is complexed with a dextran derivative of formula (I), 2 µg/ml are sufficient to attain 50% proliferation. In this case, the ratio R is equal to 3.

Example 2

PDGF-BB/DMCTrpOMe Complex

Synthesis of Carboxymethyl Dextran Modified with Tryptophan Methyl Ester (DMCTrpOMe)

The amphiphilic polymer is synthesized from a carboxymethyl dextran having a degree of substitution, in terms of carboxymethyl per saccharide unit, of 1.0 and an average molar mass of 40 000 g/mol. The tryptophan methyl ester is grafted onto the acids of this polymer according to a conventional method of coupling in water in the presence of a water-soluble carbodiimide. The degree of substitution, in terms of tryptophan per saccharide unit, is 0.3 determined by $^1$H NMR.

Preparation of the PDGF-BB/DMCTrpOMe Complex

10 μl of a solution of PDGF-BB at 0.1 mg/ml is added to 90 μl of a solution of DMCTrpOMe at 50 mg/ml. The PDGF-BB and DMCTrpOMe solutions are buffered at pH 7.4 and 300 mOsm. This solution is gently stirred for two hours at ambient temperature and then stored at 4° C.

Demonstration of the Formation of a PDGF-BB/DMCTrpOMe Complex

10 μl of the solution of the PDGF-BB/DMCTrpOMe complex described above are loaded onto an agarose gel for gel electrophoresis with immunological visualization. The compounds are migrated under the effect of an electric field (200 mA—4 hours). After migration, the PDGF-BB is transferred onto a PVDF membrane overnight, and then visualized by immunoblotting with goat anti-PGDF-BB antibodies, to which will attach anti-goat IgG secondary antibodies coupled to peroxidase, revealed by means of a substrate (5-bromo-4-chloro-3-indolyl phosphate/nitro blue tetrazolium).

The PDGF-BB/DMCTrpOMe complex migrates towards the anode. Its negative charge can be explained by the fact that its composition is much richer in DMCTrpOMe than in PDGF-BB. The control, consisting only of PDGF-BB, does not migrate.

Demonstration of the Stability of the PDGF-BB/DMCTrpOMe Complex

10 μl of a solution of PDGF-BB at 0.01 mg/ml at pH 7.4 and 10 μl of the solution of the PDGF-BB/DMCTrpOMe complex at pH 7.4 described above are placed on a shaking bench for 48 h at ambient temperature. The concentration of PDGF-BB in each of the solutions is evaluated by SDS-Page. It appears that the concentration of PDGF-BB in solution in the case of the PDGF-BB/DMCTrpOMe complex has not changed, whereas that of the solution of PDGF-BB alone has decreased.

Demonstration of the Protection of PDGF-BB Against Trypsin in this PDGF-BB/DMCTrpOMe Complex 10 μl of the solution of the PDGF-BB/DMCTrpOMe complex described above are incubated with 90 μl of a solution of trypsin at 10 ng/ml at 37° C. 10 μl samples are taken every 30 minutes and the structural integrity of the PDGF-BB is evaluated by polyacrylamide gel electrophoresis (SDS-Page) after having stopped the enzymatic reaction by adding 10 μl of a solution of indole at 10 μg/ml.

These kinetics reveal that the PDGF-BB alone is completely degraded in 1 h 30, whereas this is not the case in the PDGF-BB/DMCTrpOMe complex.

Example 3

PDGF-BB/CMCBSu Complex

Synthesis of Sulphated Carboxymethylcellulose Modified with Benzylamine (CMCBSu)

The amphiphilic polymer is synthesized from a carboxymethylcellulose having a degree of substitution, in terms of carboxymethyl per saccharide unit, of 1.2 and an average molar mass of 30 000 g/mol. The benzylamine is grafted onto the acids of this polymer according to a conventional method of coupling in water in the presence of a water-soluble carbodiimide. The degree of substitution, in terms of benzylamine per saccharide unit, is 0.2 determined by $^1$H NMR. The sulphation is carried out in the presence of an SO$_3$-pyridine complex, the degree of substitution, in terms of sulphate, is 0.30.

Preparation of the PDGF-BB/CMCBSu Complex

10 μl of a solution of PDGF-BB at 0.1 mg/ml is added to 90 μl of a solution of CMCB at 50 mg/ml. The PDGF-BB and CMCBSu solutions are buffered at pH 7.4 and 300 mOsm. This solution is gently stirred for two hours at ambient temperature and then stored at 4° C.

Demonstration of the Formation of a PDGF-BB/CMCBSu Complex

10 μl of the solution of the PDGF-BB/CMCBSu complex described above are loaded onto an agarose gel for gel electrophoresis with immunological visualization. The compounds are migrated under the effect of an electric field (200 mA—4 hours). After migration, the PDGF-BB is transferred onto a PVDF membrane overnight, and then visualized by immunoblotting with goat anti-PDGF-BB antibodies, to which will attach anti-goat IgG secondary antibodies coupled to HRP peroxidase, visualized by means of a substrate (5-bromo-4-chloro-3-indolyl phosphate/nitro blue tetrazolium).

The PDGF-BB/CMCBSu complex migrates towards the anode. This negative charge can be explained by the fact that its composition is much richer in CMCBSu than in PDGF-BB. The control, consisting only of PDGF-BB, does not migrate.

Demonstration of the Stability of the PDGF-BB/CMCBSu Complex

10 μl of a solution of PDGF-BB at 0.01 mg/ml at pH 7.4 and 10 μl of the solution of the PDGF-BB/CMCBSu complex at pH 7.4 described above are placed on a shaking bench for 48 h at ambient temperature. After centrifugation, the concentration of PDGF-BB in each of the solutions is evaluated by SDS-Page. It appears that the concentration of PDGF-BB in solution in the case of the PDGF-BB/CMCBSu complex does not change, whereas that of the solution of PDGF-BB alone has decreased.

Demonstration of the Protection of the PDGF-BB Against Trypsin in this PDGF-BB/CMCBSu Complex 10 μA of the solution of the PDGF-BB/CMCBSu complex described above are incubated with 90 μl of a solution of trypsin at 10 ng/ml at 37° C. 10 μl samples are taken every 30 minutes and the structural integrity of the PDGF-BB is evaluated by polyacrylamide gel electrophoresis (SDS-Page) after having stopped the enzymatic reaction by adding 10 μl of a solution of indole at 10 μg/ml.

These kinetics reveal that the PDGF-BB alone is completely degraded in 1 h 30, whereas this is not the case in the PDGF-BB/CMCBSu complex.

Counter Example 1

PDGF-BB/CMCB Complex

Synthesis of Carboxymethylcellulose Modified with Benzylamine (CMCB)

The amphiphilic polymer is synthesized from a carboxymethylcellulose having a degree of substitution, in terms of carboxymethyl per saccharide unit, of 1.2 and an average molar mass of 30 000 g/mol. The benzylamine is grafted onto the acids of this polymer according to a conventional method of coupling in water in the presence of a water-soluble carbodiimide. The degree of substitution, in terms of benzylamine per saccharide unit, is 0.2 determined by $^1H$ NMR.

Preparation of the PDGF-BB/CMCB Complex

10 μl of a solution of PDGF-BB at 0.1 mg/ml are added to 90 μl of a solution of CMCB at 50 mg/ml. The PDGF-BB CMCB solutions are buffered at pH 7.4 and 300 mOsm. This solution is gently stirred for two hours at ambient temperature and then stored at 4° C.

Demonstration of the Non-Formation of PDGF-BB/CMCB Complex

10 μl of the solution of the PDGF-BB/CMCB complex described above are loaded onto an agarose gel for gel electrophoresis with immunological visualization. The compounds are migrated under the effect of an electric field (200 mA—4 hours). After migration, the PDGF-BB is transferred onto a PVDF membrane overnight, and then visualized by immunoblotting with goat anti-PDGF-BB antibodies, to which will attach anti-goat IgG secondary antibodies coupled to HRP peroxidase, visualized by means of a substrate (5-bromo-4-chloro-3-indolyl phosphate/nitro blue tetrazolium).

The visualization does not show any migration of the PDGF-BB alone with the amphiphilic polymer. There has been no formation of complex between the CMCB and the PDGF-BB.

The invention claimed is:

1. A composition comprising an amphiphilic polysaccharide-PDGF complex solubilized in an aqueous medium, wherein:

the amphiphilic polysaccharide comprises a hydrophilic polysaccharide backbone functionalized with hydrophobic substituents and hydrophilic substituents according to the following general formula:

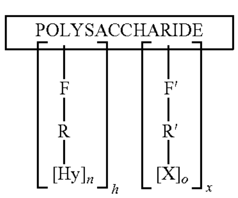

R and R' being a bond or a chain comprising between 1 and 18 carbons, optionally branched, unsaturated, and/or containing one or more heteroatoms, R and R' being identical to or different from one another, F and F' being selected from the group consisting of an ester, an amide, a carbamate, and an ether, F and F' being identical to or different from one another, X being a hydrophilic group that is a carboxylate, Hy being a hydrophobic group that is selected from the group consisting of:

a $C_8$ to $C_{30}$ linear or branched alkyl, optionally unsaturated and/or containing one or more heteroatoms, a $C_8$ to $C_{18}$ linear or branched alkylaryl or arylalkyl, optionally unsaturated and/or containing one or more heteroatoms, and an optionally unsaturated $C_8$ to $C_{30}$ polycycle, n and o are between 1 and 3, h represents the molar fraction of hydrophobic groups to saccharide units and is between 0.01 and 0.5, x represents the molar fraction of hydrophilic groups to saccharide units and is between 0 and 2.0, and the PDGF is a platelet-derived growth factor.

2. The composition according to claim 1, wherein PDGF is a human recombinant PDGF containing two B chains.

3. The composition according to claim 1, wherein the polysaccharide substituents are distributed randomly.

4. The composition according to claim 1, wherein the polysaccharide is selected from the group consisting of hyaluronans, alginates, chitosans, galacturonans, chondroitin sulphate, dextrans and celluloses.

5. The composition according to claim 1, wherein the polysaccharide is carboxymethylcellulose.

6. The composition according to claim 1, wherein the polysaccharide is a dextran functionalized with a carboxylate.

7. The composition according to claim 1, wherein the polysaccharide is selected from the group consisting of hyaluronans, alginates and chitosans.

8. The composition according to claim 1, wherein the hydrophobic group Hy is selected from the group consisting of fatty acids, fatty alcohols, fatty amines, benzyl amines, cholesterols and phenols.

9. The composition according to claim 1, wherein the amphiphilic polysaccharide-PDGF complex is reversibly formed.

10. The composition according to claim 1, wherein a weight ratio of PDGF to amphiphilic polysaccharide is between 1/5 and 1/5000.

11. The composition according to claim 1, wherein a weight ratio of PDGF to amphiphilic polysaccharide is between 1/100 and 1/5000.

12. The composition according to claim 1, wherein a weight ratio of PDGF to amphiphilic polysaccharide is between 1/300 and 1/700.

13. A method of preparing the composition according to claim 1, comprising combining the polysaccharide, PDGF, and the aqueous medium in the absence of an organic solvent that may denature the protein.

14. The composition according to claim 1, wherein the composition comprises 100 μg per ml of PDGF.

15. A method of treating a diabetic ulcer comprising topically applying the composition according to claim 1 to the diabetic ulcer.

16. The composition according to claim 1, wherein the hydrophobic group Hy is tryptophan or an ester or salt of tryptophan.

17. The composition according to claim 1, wherein the composition is formulated as a spray.

* * * * *